(12) United States Patent
Hsiao

(10) Patent No.: US 8,066,420 B2
(45) Date of Patent: Nov. 29, 2011

(54) AROMA DIFFUSING NIGHT LAMP SYSTEM HAVING AN ANGLE-ADJUSTABLE ELECTRIC PLUG

(76) Inventor: Ming Jen Hsiao, Toufen (TW)

( * ) Notice: Subject to any disclaimer, the term of this patent is extended or adjusted under 35 U.S.C. 154(b) by 124 days.

(21) Appl. No.: 12/698,610

(22) Filed: Feb. 2, 2010

(65) Prior Publication Data
US 2011/0110119 A1 May 12, 2011

Related U.S. Application Data

(63) Continuation-in-part of application No. 12/616,560, filed on Nov. 11, 2009, now abandoned.

(51) Int. Cl.
*H01R 33/00* (2006.01)
*H01R 39/00* (2006.01)
(52) U.S. Cl. ............... 362/640; 362/649; 362/249.07; 362/285; 439/22

(58) Field of Classification Search .......... 362/640–641, 362/644, 649, 652, 249.07, 285, 287, 288; 439/22, 18
See application file for complete search history.

(56) References Cited

U.S. PATENT DOCUMENTS

| | | | | |
|---|---|---|---|---|
| 3,443,083 A | * | 5/1969 | Curran | 362/643 |
| 4,346,059 A | * | 8/1982 | Spector | 422/125 |
| 6,638,074 B1 | * | 10/2003 | Fisher | 439/22 |
| 7,712,915 B2 | * | 5/2010 | Liu | 362/183 |
| 7,810,985 B2 | * | 10/2010 | Chien | 362/641 |

* cited by examiner

*Primary Examiner* — Ali Alavi
(74) *Attorney, Agent, or Firm* — Chun-Ming Shih

(57) ABSTRACT

An aroma diffusing night lamp system having the characteristics of high level of safety and installation angle adjustability is disclosed to include a lamp socket, a light emitting device mounted in the top side of the lamp socket, an electric plug rotatably coupled to the lamp socket and a lampshade surrounding the light emitting device and having a top trough that holds an aromatic substance that gives off a pleasant smell when heated by heat energy from the light emitting device during its operation.

9 Claims, 9 Drawing Sheets

US 8,066,420 B2

AROMA DIFFUSING NIGHT LAMP SYSTEM HAVING AN ANGLE-ADJUSTABLE ELECTRIC PLUG

CROSS-REFERENCE TO RELATED APPLICATION

This invention is a continuation-in-part of U.S. patent application Ser. No. 12/616,560, entitled "Aroma diffusing night lamp system", filed on Nov. 11, 2009 now abandoned.

BACKGROUND OF THE INVENTION

1. Field of the Invention

The present invention relates to scent releasing devices and more specifically, to an aroma diffusing night lamp system that combines a night lamp unit and an aroma diffuser unit together and that uses an angle-adjustable electric plug to obtain the necessary working power supply.

2. Description of the Related Art

Conventional night lamp does not allow adjustment of the angular position of the two parallel metal prongs of their electric plugs to fit different indoor installation requirements.

There are night lamps with an added aroma diffusing function. These night lamps combine an angle-adjustable night lamp unit and an aroma diffuser unit. When the night lamp unit of a night lamp is connected to a city power supply outlet, the radiating heat from the night lamp unit heats an aromatic substance, for example, essential oil in the aroma diffuser unit into vapor, providing a romantic atmosphere and enhancing the value of use of the night lamp.

Although conventional aroma diffusing night lamps allow adjustment of the installation angle of the night lamp unit, their angle-adjustable structure wears quickly with use or is difficult to be adjusted to the accurate angle. After installation, the applied essential oil may fall from the lampshade accidentally.

Further, regular aroma diffusing night lamps commonly use an incandescent lamp bulb to emit light and to heat the supplied aromatic substance. The heating efficiency of an incandescent lamp is low. Further, the aroma diffuser unit of a regular aroma diffusing night lamp is less stable. In consequence, a gap may be produced in the electric conducting structure, affecting the performance of electric conductivity. Further, regular aroma diffusing night lamps have no means to seal the electric conducting component parts. If the aromatic fluid leaks out, a short circuit accident may occur.

Further, some known aroma diffusing nigh lamps use a lampshade prepared from a light-transmissive heat-resisting hard material such as ceramic or glass. During installation, small retaining and/or fastening members are used to affix the lampshade in place. The use of these retaining and/or fastening members may cause the lampshade to break, shortening the night lamp lifespan and threatening user safety.

SUMMARY OF THE INVENTION

The present invention has been accomplished to provide an aroma diffusing night lamp system having an angle-adjustable electric plug, which eliminates the drawbacks of the aforesaid prior art designs. It is therefore the main object of the present invention to provide an aroma diffusing night lamp system having an angle-adjustable electric plug, which is durable and safe in use, avoiding breaking of the lampshade and allowing adjustment of the angular position of the electric plug.

To achieve this and other objects of the present invention, an aroma diffusing night lamp system comprises a lamp socket having a round hole on one side thereof, a light emitting device mounted in the top side of the lamp socket, a lampshade fastened to the lamp socket around the light emitting device, the lampshade having a top trough located on the top side thereof for holding an aromatic substance, a bottom edge located on the bottom side thereof and a through hole cut through the bottom edge and coupled to the lamp socket, and an electric plug coupled and rotatable relative to the lamp socket and adapted for electrically connecting the lamp socket to an external city power supply outlet. The electric plug comprises an electric plug body having a cylindrical rear side, a first shaft holder shell and a second shaft holder shell. The cylindrical rear side has a small diameter section and a big diameter section for connection to the lamp socket. The first shaft holder shell has two arched arms defining an arched groove. The second shaft holder shell has two arched arms defining an arched groove. The arched arms of the first shaft holder shell are respectively abutted against the arched arms of the second shaft holder shell around the small diameter section of the cylindrical rear side of the electric plug body and fastened to the round hole of the lamp socket to keep the arched grooves of the first shaft holder shell and second shaft holder shell in friction engagement with the big diameter section of the cylindrical rear side of the electric plug body.

In one embodiment of the present invention, the lamp socket comprises a first socket shell, a second socket shell and a power switch. The first socket hell has a retaining rod perpendicularly extended from the periphery thereof. The second socket shell has a retaining rod perpendicularly extended from the periphery thereof. The first socket shell and the second socket shell are fastened together to hold the light emitting device in place. The power switch is mounted in one side of the second socket shell.

Further, the lamp socket is mounted with a gasket ring that is stopped against the bottom edge of the lampshade. The retaining rods of the first socket shell and second socket shell are inserted through the through hole on the bottom edge of the lampshade and stopped at the top side of the bottom edge of the lampshade after rotation of lamp socket relative to the lampshade through an angle.

Further, the gasket ring has a bottom ring portion, a top ring portion, an upright stop wall and a hole. The top ring portion is located on the top side of the bottom ring portion. The top ring portion has a relatively smaller diameter than the bottom ring portion so that the periphery of the top ring portion defines the upright stop wall. The hole of the gasket ring extends through the top ring portion and the bottom ring portion at the center. The upright stop wall has a diameter fitting the diameter of the through hole on the bottom edge of the lampshade. The gasket ring is mounted around an upper part of the lamp socket below the retaining rods of the first socket shell and the second socket shell and stopped at the top side of the bottom edge of the lampshade after insertion of the retaining rods of the first socket shell and the second socket shell upwardly through the through hole on the bottom edge of the lampshade and rotation of the lamp socket relative to the lampshade through an angle.

The electric plug further comprises a gear wheel located on the cylindrical rear side of the electric plug body. The lamp socket has a damping spring leaf mounted in a locating groove in the round hole thereof. The damping spring leaf has a protruding damping portion located on a middle part thereof stopped against the toothed periphery of the gear wheel. Further the damping spring leaf has W-shaped configuration.

The locating groove of the lamp socket has a W-shaped configuration fitting the W-shaped configuration of the damping spring leaf.

Further, the electric plug body has a plurality of retaining blocks equiangularly spaced around the cylindrical rear side thereof for securing the gear wheel. The retaining blocks of the electric plug body have a triangular shape. The gear wheel is a gear ring, having a plurality of triangular retaining grooves equiangularly arranged on the inner diameter thereof and respectively forced into engagement with the triangular retaining blocks of the electric plug.

Further, the lamp socket comprises a spring holder groove, a set of first metal conducting plates arranged at one lateral side relative to the spring holder groove and electrically connected to one of the positive and negative poles of the light emitting device, a set of second metal conducting plates arranged at an opposite lateral side relative to the spring holder groove and electrically connected to the other one of the positive and negative poles of the light emitting device, a spring member mounted in the spring holder groove, and a metal ball supported on the spring member. The power switch has a cone adapted for moving the metal ball between a first position to electrically connect the set of first metal conducting plates and the set of second metal conducting plates and a second position to electrically disconnect the set of first metal conducting plates from the set of second metal conducting plates.

In conclusion, the invention utilizes a light emitting device to heat the applied aromatic substance into vapor, allows accurate adjustment of the angular position of the electric plug relative to the electric socket, and avoids breaking of the lampshade.

DETAILED DESCRIPTION OF THE PREFERRED EMBODIMENT

Figure 1:
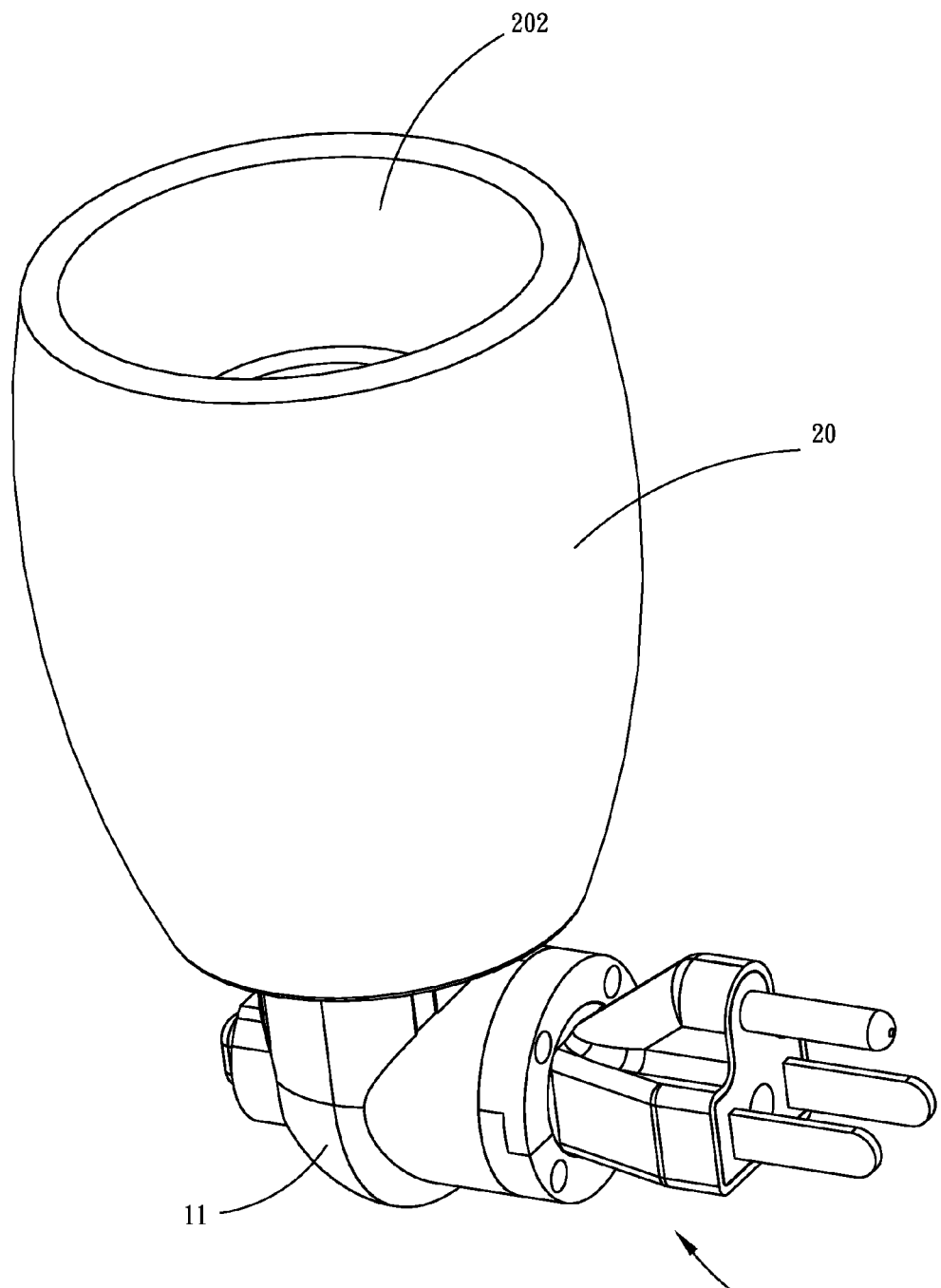
FIG. 1 is an elevational view of an aroma diffusing night lamp system in accordance with a first embodiment of the present invention.
Figure 2:
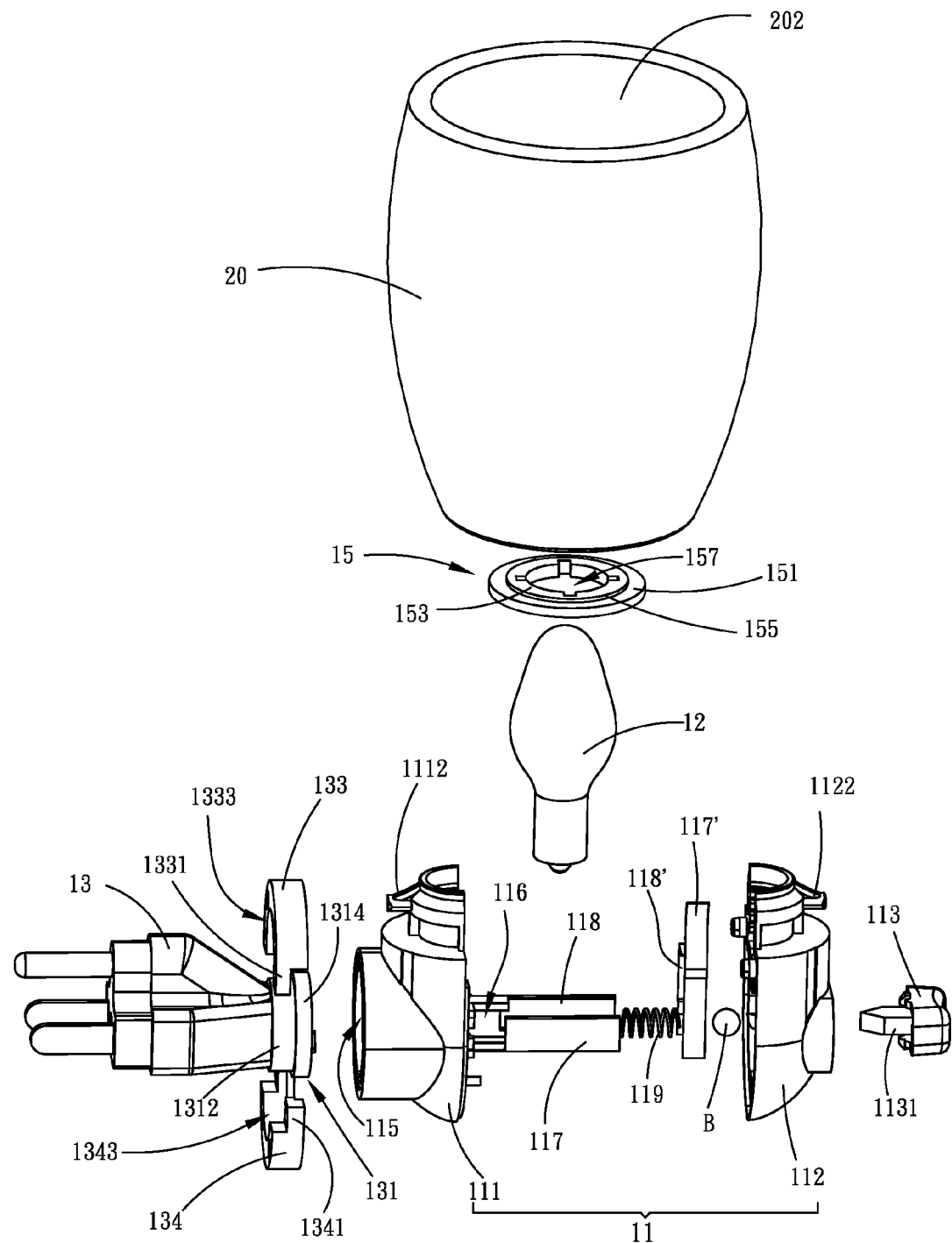
FIG. 2 is an exploded view of the aroma diffusing night lamp system in accordance with the first embodiment of the present invention.
Figure 3:
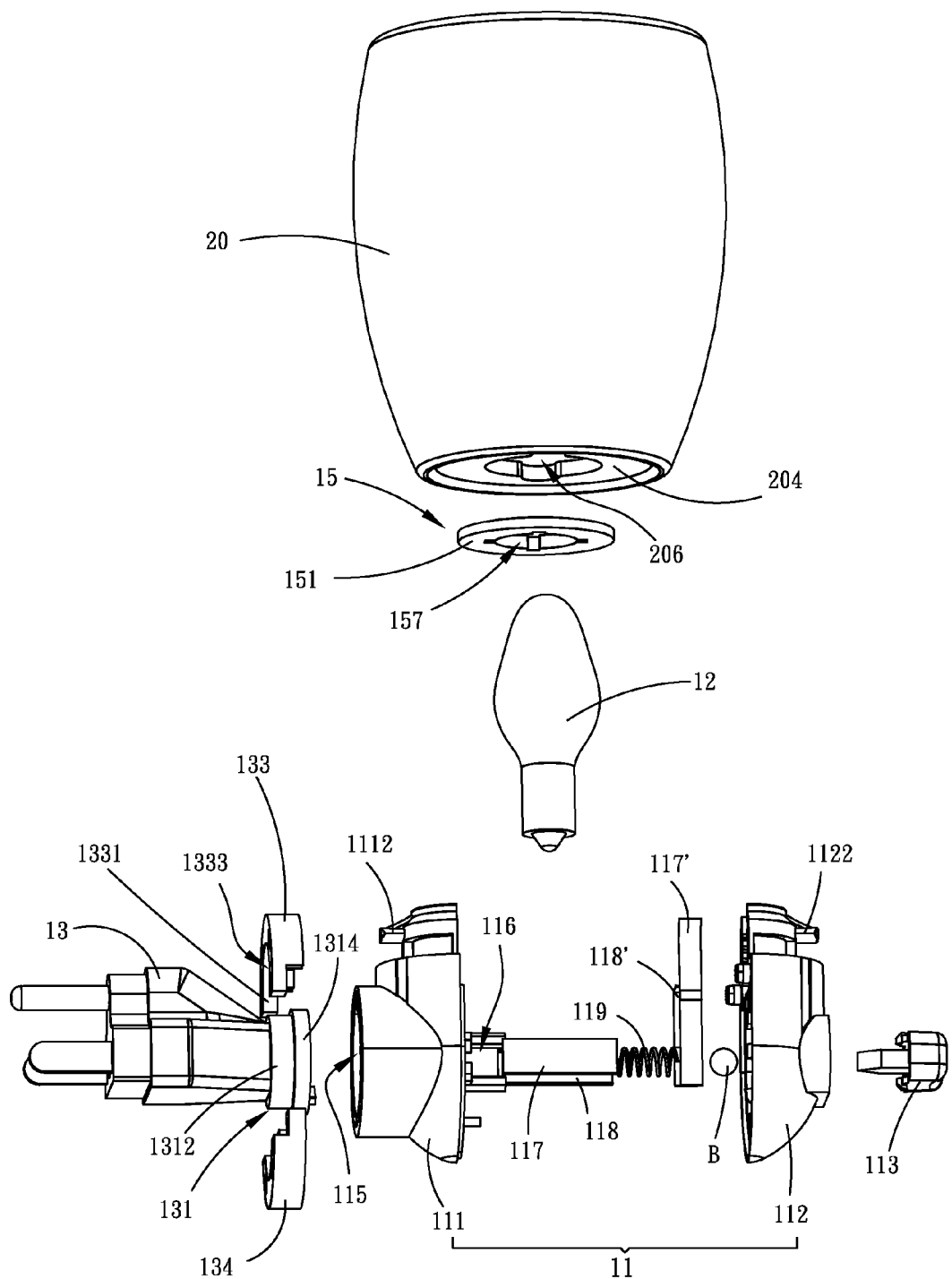
FIG. 3 is a schematic top view of the aroma diffusing night lamp system in accordance with the first embodiment of the present invention.
Figure 4:
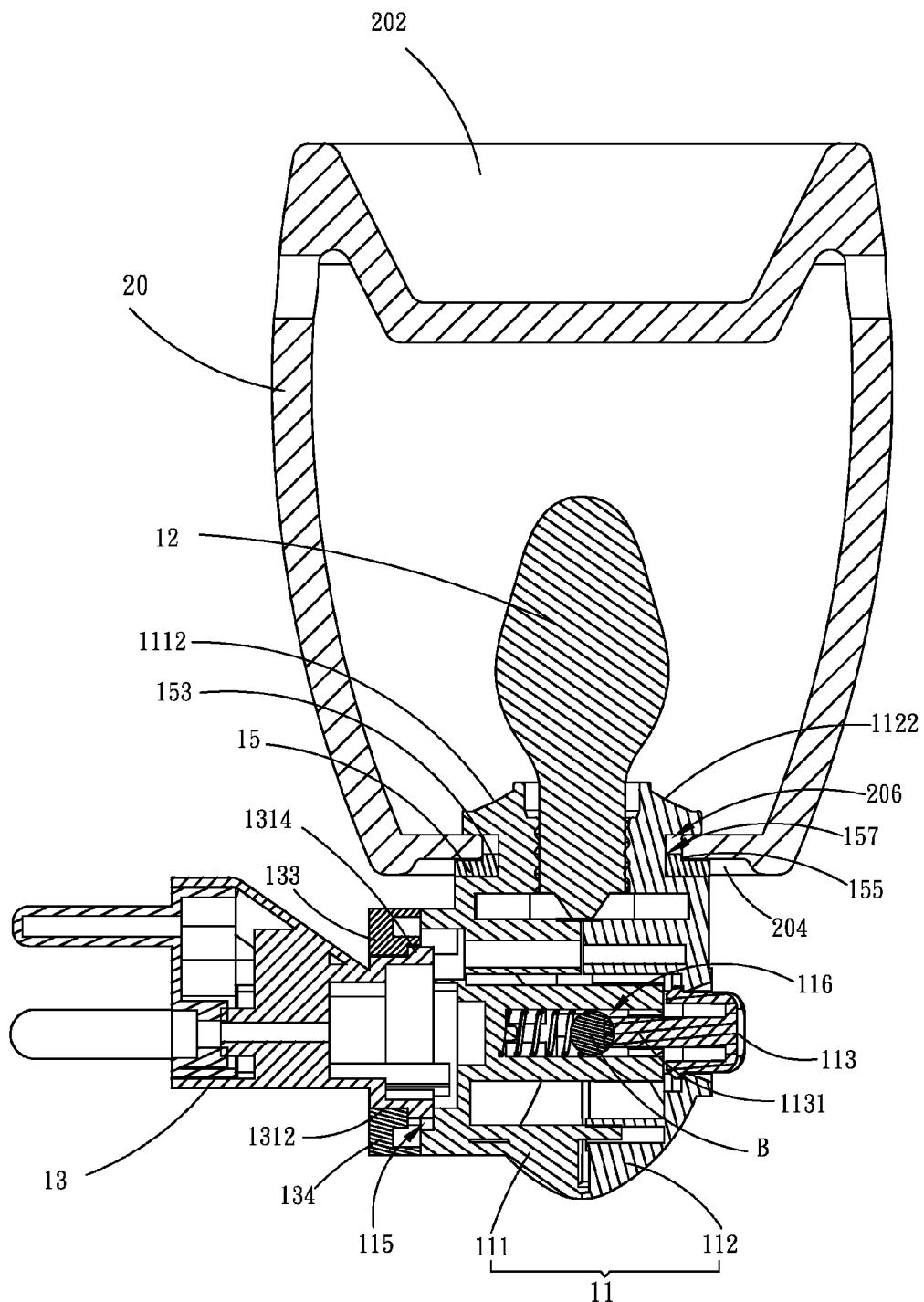
FIG. 4 is a schematic sectional view of the aroma diffusing night lamp system in accordance with the first embodiment of the present invention.

Referring to FIGS. 1-4, an aroma diffusing night lamp system having an angle-adjustable electric plug in accordance with a first embodiment of the present invention is shown comprising a lamp socket 11, a light emitting device 12, an electric plug 13 and a lampshade 20. The aroma diffusing night lamp system is safe and durable in use and allows adjustment of the installation angle of the electric plug 13.

The lamp socket 11 has a round hole 115 on one side thereof. The light emitting device 12 is mounted in the top side of the lamp socket 11. The lampshade 20 has a shadow fluid trough 202 defined in the top side thereof, a bottom edge 204 located on the bottom side thereof and a through hole 206 cut through the center of the bottom edge 204. An aromatic substance (such as essential oil, fragrant wax or the like) is put in the shadow fluid trough 232. By means of the through hole 236 on the bottom edge 234 of the lampshade 23, the lampshade 23 is coupled to the lamp socket 11 and surrounds the light emitting device 12.

Further, the electric plug 13 comprises an electric plug body 131 having a cylindrical rear side formed of a small diameter section 1312 and a big diameter section 1314 for connection to the lamp socket 11, a first shaft holder shell 133 and a second shaft holder shell 134. The first shaft holder shell 133 has two arched arms 1331, defining an arched groove 1333. The second shaft holder shell 134 has two arched arms 1341, defining an arched groove 1343. The arched arms 1333 of the first shaft holder shell 133 are respectively abutted against the arched arms 1343 of the second shaft holder shell 134 around the small diameter section 1312 of the stepped cylindrical rear side of the electric plug body 131 to keep the arched grooves 1333 and 1343 in friction engagement with the big diameter section 1314 of the stepped cylindrical rear side of the electric plug body 131. Thus, the electric plug body 131 is secured and rotatable relative to the first shaft holder shell 133 and the second shaft holder shell 134. After rotation, the friction force between the stepped cylindrical rear side of the electric plug body 131 and the first and second shaft holder shells 133 and 134 secures the electric plug body 131 to the first and second shaft holder shells 133 and 134 firmly in position. After coupling of the electric plug body 131 with the first and second shaft holder shells 133 and 134 to the round hole 115 of the electric socket 11, the electric plug 13 can be rotated relative to the first and second shaft holder shells 133 and 134 and the electric socket 11 to fit different installation requirements. Further, the aforesaid light emitting device 12 is electrically connected to the electric plug 13. After connection of the electric plug 13 to power supply, the light emitting device 12 is turned on to emit light through the lampshade 20, and at the same time the aromatic substance (such as essential oil, fragrant wax or the like) is heated by heat energy released from the light emitting device 12 to give off a pleasant smell.

The lamp socket 11 comprises two symmetrical socket shells, namely, first and second socket shells 111 and 112, and a power switch 113. The first socket shell 111 has a retaining rod 1112 perpendicularly extended from the periphery thereof. The second socket shell 112 has a retaining rod 1122 perpendicularly extended from the periphery thereof. The two symmetrical socket shells 111 and 112 surround the light emitting device 12, holding the light emitting device 12 firmly in position. The power switch 113 is installed in the second socket shell 112 and exposed to the outside. After the electric plug 13 is connected to an external power source and the power switch 113 is switched on, the lamp socket 11 and light emitting device 12 are electrically connected to emit light and to produce heat. On the contrary, when the power switch 113 is switched off, the lamp socket 11 and light emitting device 12 are electrically disconnected. The aforesaid round hole 115 is located on the first socket shell 111 at one side opposite to the power switch 113.

Referring to FIGS. 3 and 4 again, the aroma diffusing night lamp system further comprises a gasket ring 15 mounted on the lamp socket 11 and stopped between a part of the lamp socket 11 and the bottom edge 204 of the lampshade 20. The gasket ring 15 has a bottom ring portion 151, a top ring portion 153, an upright stop wall 155 and a hole 157. The top ring portion 153 is located on the top side of the bottom ring portion 151. The top ring portion 153 has a relatively smaller diameter than the bottom ring portion 151 so that the periphery of the top ring portion 153 defines the upright stop wall 155. The hole 157 cut through the top ring portion 153 and the bottom ring portion 151 at the center. The gasket ring 15 is prepared from an elastic material such as rubber, silicon rubber or elastic plastics. The diameter of the upright stop wall 155 fits the diameter of the through hole 206 on the bottom edge 204 of the lampshade 20. After mounting of the gasket ring 15 on the upper part of the lamp socket 11, the retaining rods 1112 and 1122 are upwardly inserted with the two symmetrical socket shells 111 and 112 of the lamp socket 11 through the through hole 206 on the bottom edge 204 of the lampshade 20 to force the top ring portion 153 into the through hole 206 and to stop the bottom ring portion 151 against the bottom edge 204, and then the lamp socket 11 is rotated through an angle to have the retaining rods 1112 and 1122 to be stopped at the top side of the bottom edge 204 of the lampshade 20. Thus, the lamp socket 11 and the lampshade 20 are secured together, and the upright stop wall 155 is kept engaged in the through hole 206 for enabling the contact force between the lamp socket 11 and the lampshade 20 to be evenly distributed through the lamp socket 11 and the lampshade 20, avoiding concentration of shear stress or flexural shear stress.

Figure 5:
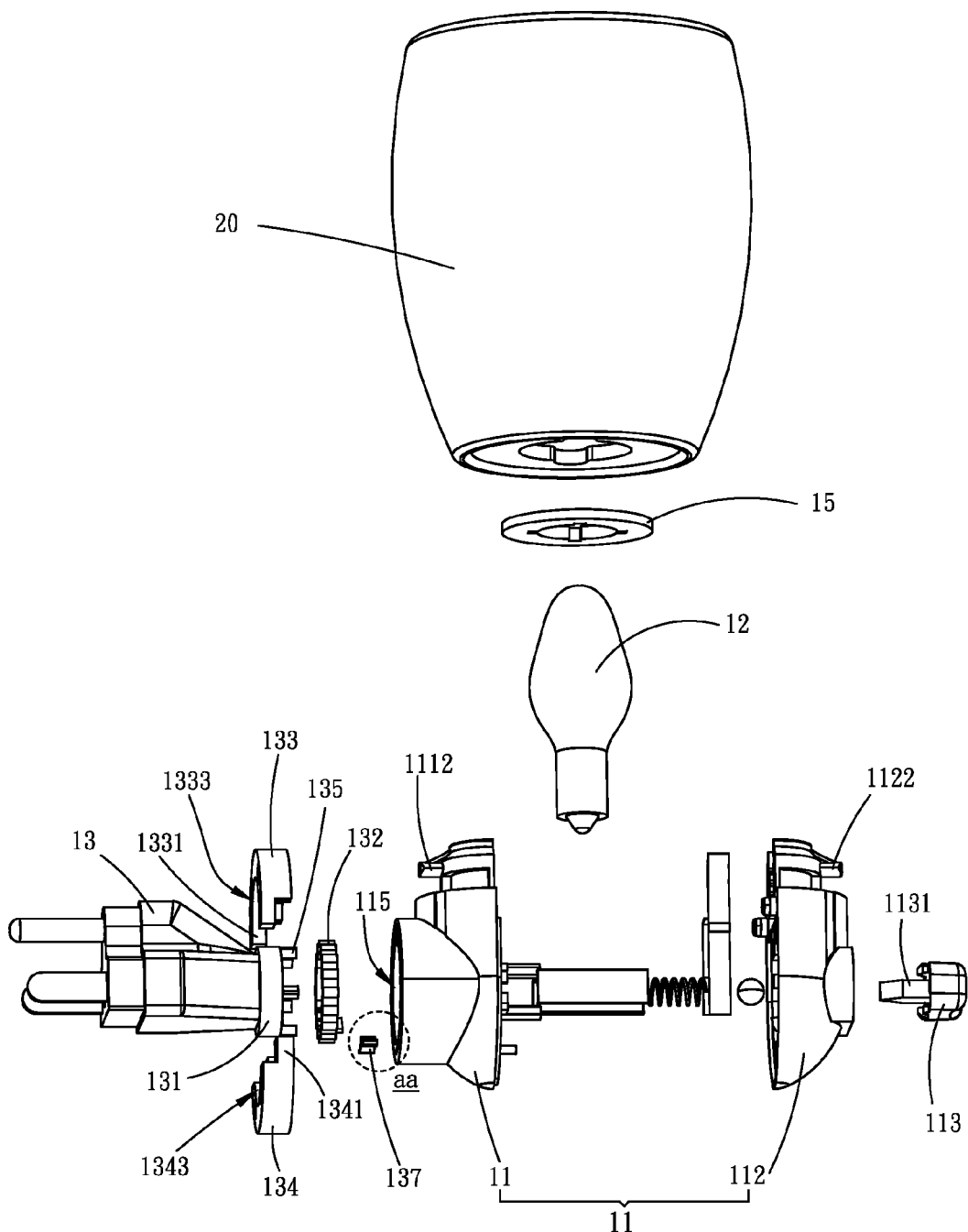
FIG. 5 is an elevational view of an aroma diffusing night lamp system in accordance with a second embodiment of the present invention.
Figure 6:
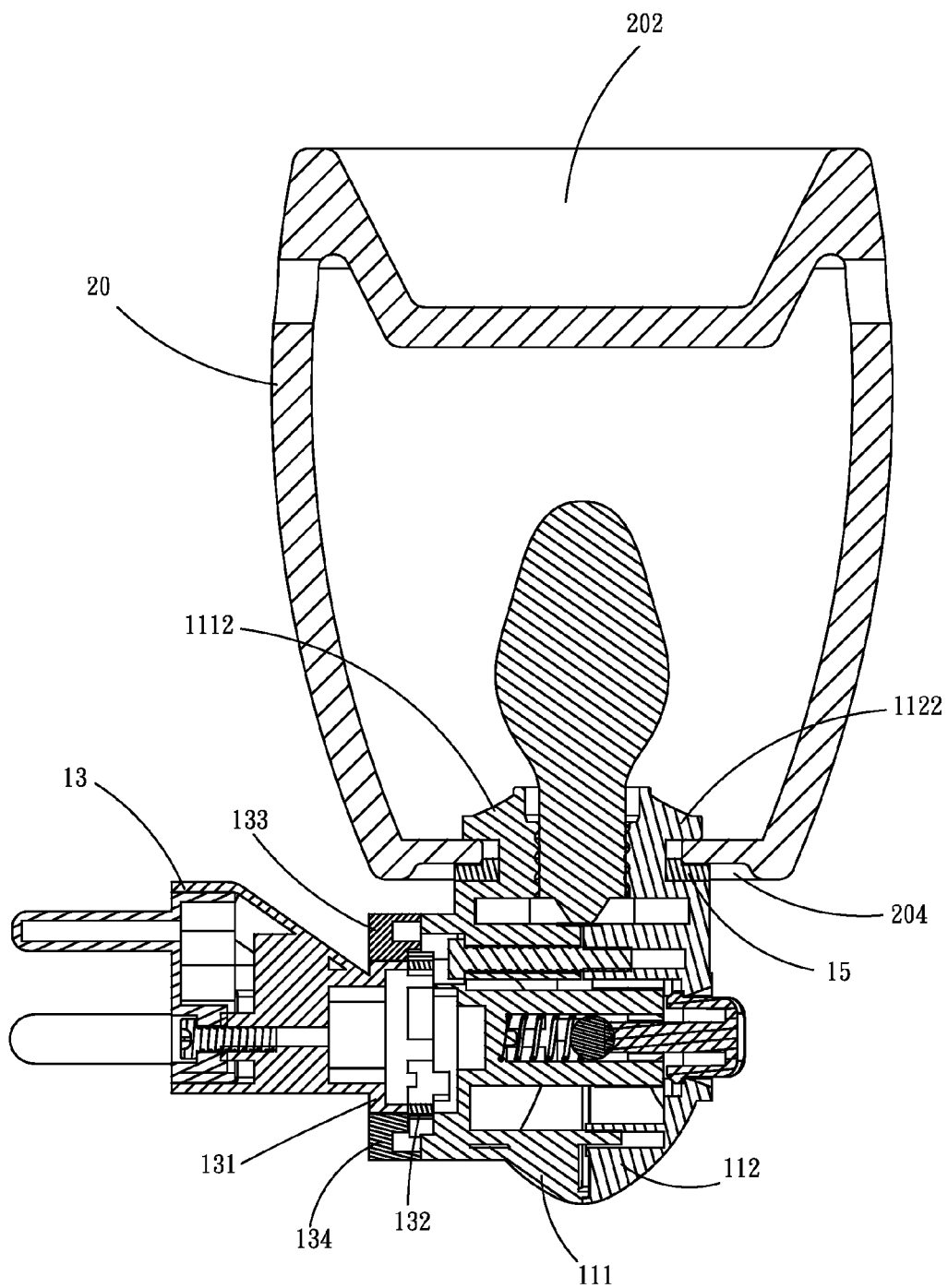
FIG. 6 is a schematic sectional view of the aroma diffusing night lamp system in accordance with the second embodiment of the present invention.
Figure 7:
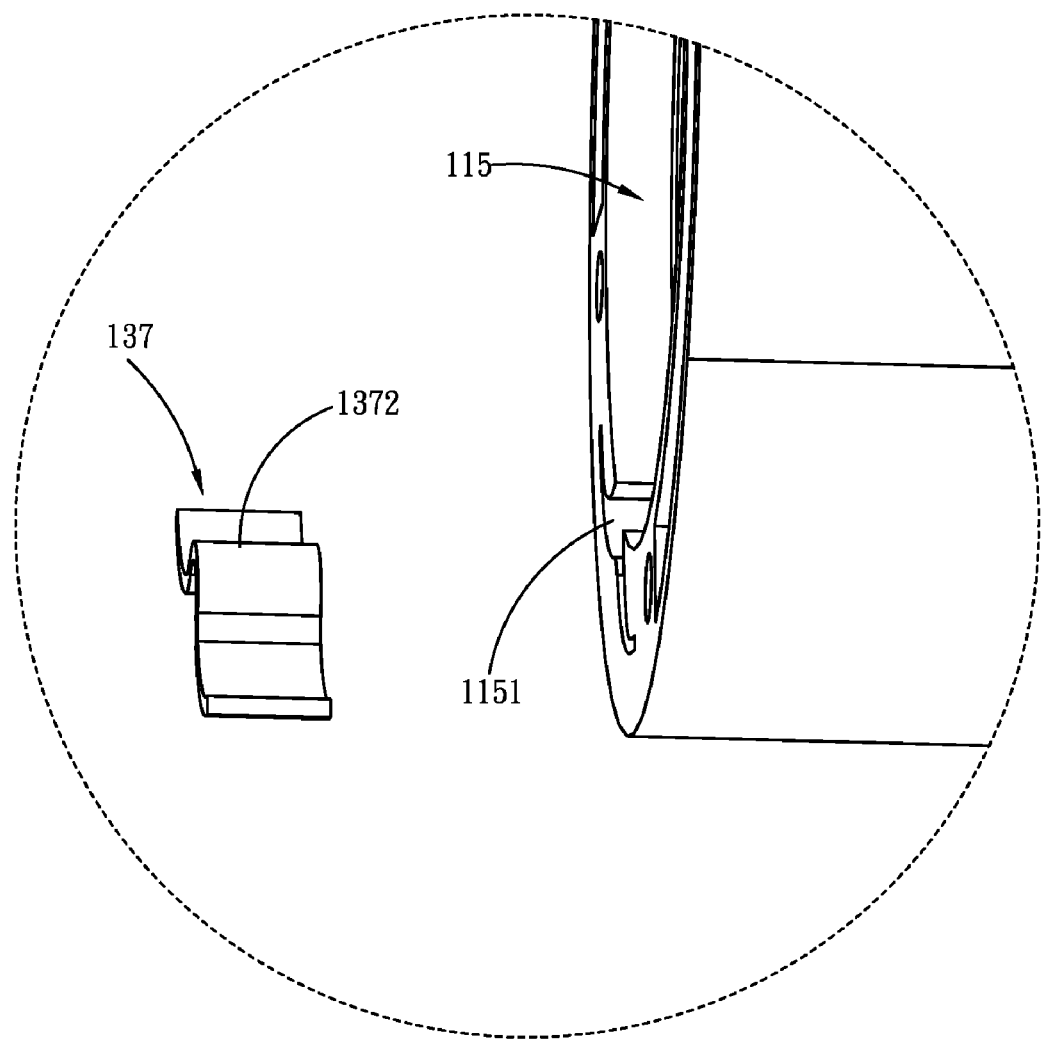
FIG. 7 is an enlarged view of part aa of FIG. 5.

FIGS. 5~7 show an aroma diffusing night lamp system having an angle-adjustable electric plug in accordance with a second embodiment of the present invention. This second embodiment is substantially similar to the aforesaid first embodiment with the exception that the electric plug 13 of this second embodiment further comprises a gear wheel 132 arranged on the cylindrical rear side of the electric plug body 131 to replace the aforesaid big diameter section 1314 for connection to the lamp socket 11; the lamp socket 11 further comprises a damping spring leaf 137. The damping spring leaf 137 has a W-shaped configuration and a protruding damping portion 1192 on the middle. The socket shell 111 further has a locating groove 1151 disposed in the round hole 115 and configured to fit the W-shaped configuration of the damping spring leaf 117. After mounting of the damping spring leaf 117 in the locating groove 1151 inside the round hole 115, the protruding damping portion 1172 of the damping spring leaf 117 is kept suspending in the round hole 115. When the gear wheel 132 of the electric plug 13 is partially inserted into the round hole 115 of the socket shell 111, the protruding damping portion 1172 of the damping spring leaf 117 is stopped against the toothed periphery of the gear wheel 132 (see FIGS. 8 and 9), holding the gear wheel 132 in place and allowing rotation of the gear wheel 132 with the electric plug body 131 relative to the lamp socket 11 to adjust the angle of the electric plug 13. Thus, the user can adjust the angle of the electric plug 13 relative to the electric socket 11 accurately.

Figure 8:
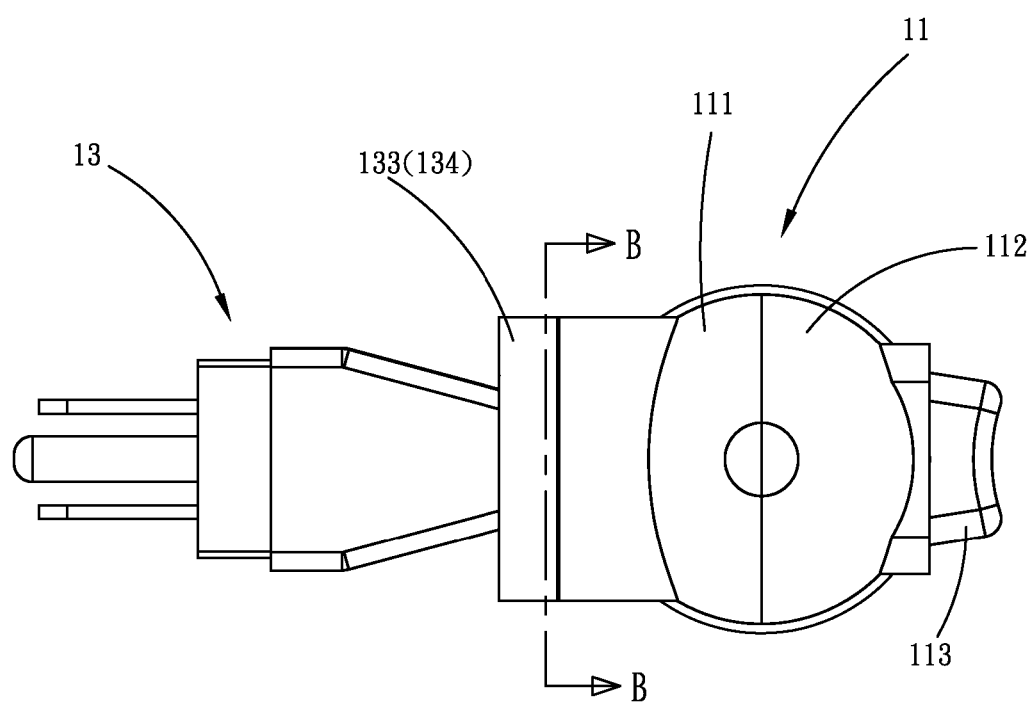
FIG. 8 is a schematic bottom view of the aroma diffusing night lamp system in accordance with the second embodiment of the present invention.
Figure 9:
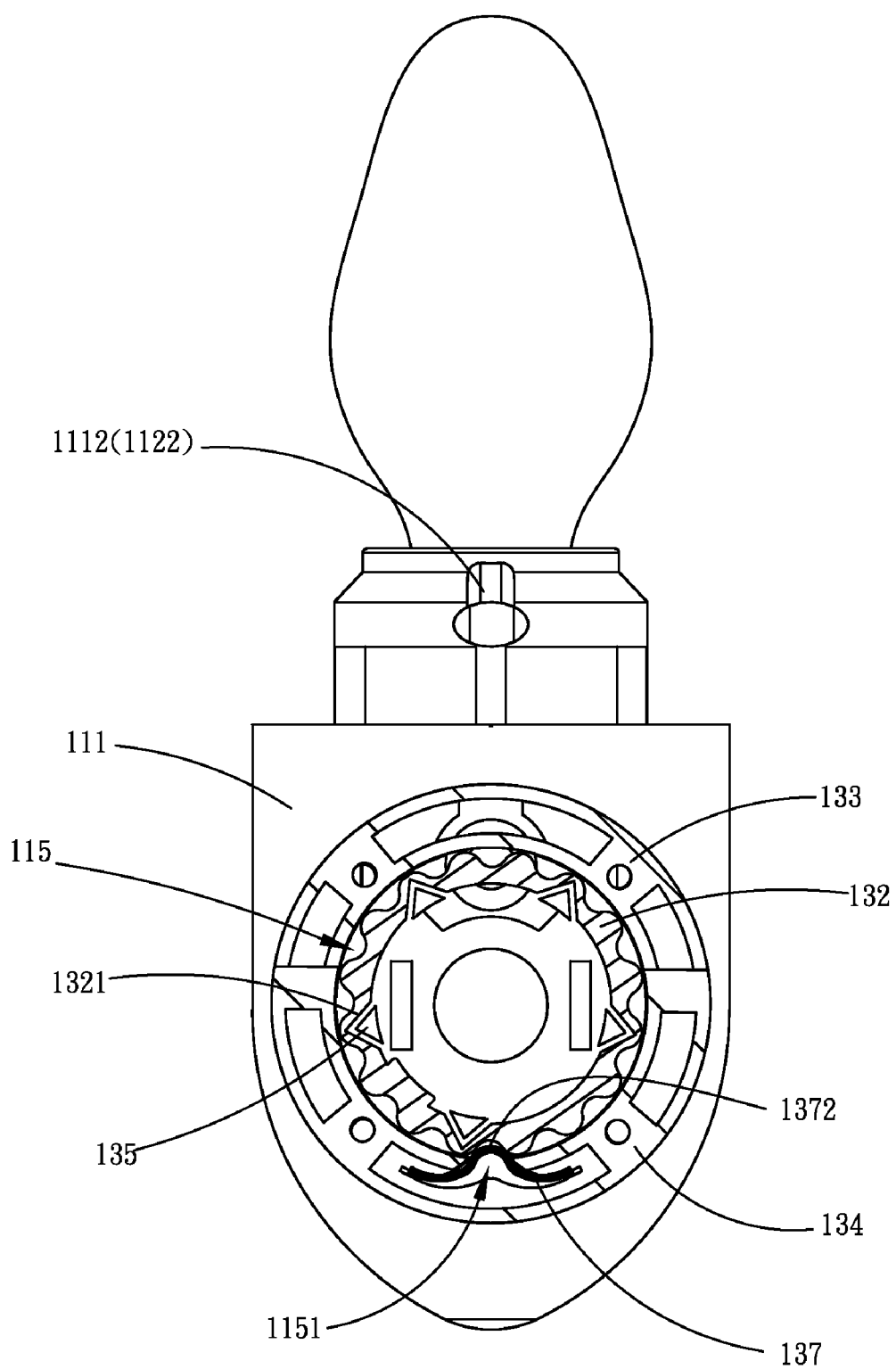
FIG. 9 is a sectional view taken along line B-B of FIG. 8.

Referring to FIGS. 8 and 9 and FIG. 5 again, the cylindrical rear side of the electric plug body 131 of the electric plug 13 has a plurality of triangular retaining blocks 135 equiangularly spaced around the cylindrical rear side thereof. The gear wheel 135 is a gear ring, having a plurality of triangular retaining grooves 1321 equiangularly arranged on the inner diameter thereof and respectively forced into engagement with the triangular retaining blocks 135 of the electric plug body 131 of the electric plug 13. After installation of the gear wheel 132 in the cylindrical rear side of the electric plug body 131 of the electric plug 13, the electric plug 13 can then be fastened with the shaft holder shells 133 and 134 to the lamp socket 11 and then rotated relative to the lamp socket 11 to the desired angle. By means of using the damping spring leaf 137 to stop the gear wheel 132, the structure is strong and does not wear quickly with use.

In either of the aforesaid first and second embodiments, the lamp socket 11 further comprises a spring holder hole 116, a pair of first metal conducting plates 117 and 117', a pair of second metal conducting plates 118 and 118', a spring member 119 and a metal ball B. The spring member 119 is mounted in the spring holder hole 116. The pair of first metal conducting plates 117 and 117' are electrically connected and arranged at one lateral side relative to the spring holder hole 116. The pair of second metal conducting plates 118 and 118' are arranged in parallel at the other lateral side relative to the spring holder hole 116. The pair of first metal conducting plates 117 and 117' and the pair of second metal conducting plates 118 and 118' are respectively electrically connected to the positive pole and negative pole of the light emitting device 12. The metal ball B is set between the spring member 119 and the power switch. The power switch 113 further has a cone 1131 adapted for shifting the metal ball B. Thus, when the lamp socket 11 is assembled, and the power switch 113 is switched on, the cone 1131 forces the metal ball B to contact the pair of second metal conducting plates 118 and 118' and to compress the spring member 119, closing the circuit of the pair of first metal conducting plates 117 and 117' and the pair of second metal conducting plates 118 and 118', and therefore the light emitting device 12 is turned on to emit light and to heat the aromatic substance (such as essential oil, fragrant wax or the like) in the shadow fluid trough 232 of the lampshade 20.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. An aroma diffusing night lamp system, comprising:
 a lamp socket, said lamp socket having a round hole on one side thereof;
 a light emitting device mounted in a top side of said lamp socket;
 a lampshade fastened to said lamp socket around said light emitting device, said lampshade having a top trough located on a top side thereof for holding an aromatic substance, a bottom edge located on a bottom side thereof and a through hole cut through said bottom edge and coupled to said lamp socket; and
 an electric plug coupled and rotatable relative to said lamp socket and adapted for electrically connecting said lamp socket to an external city power supply outlet, said electric plug comprising an electric plug body having a cylindrical rear side, a first shaft holder shell and a second shaft holder shell, said cylindrical rear side having a small diameter section and a big diameter section for connection to said lamp socket, said first shaft holder shell having two arched arms defining an arched groove, said second shaft holder shell having two arched arms defining an arched groove, the arched arms of said first shaft holder shell being respectively abutted against the arched arms of said second shaft holder shell around said small diameter section of said cylindrical rear side of said electric plug body and fastened to the round hole of said lamp socket to keep the arched grooves of said first shaft holder shell and said second shaft holder shell in friction engagement with said big diameter section of said cylindrical rear side of said electric plug body.

2. The aroma diffusing night lamp system as claimed in claim 1, wherein said lamp socket comprises a first socket shell, a second socket shell and a power switch, said first socket hell having a retaining rod perpendicularly extended from the periphery thereof, said second socket shell having a retaining rod perpendicularly extended from the periphery thereof, said first socket shell and said second socket shell being fastened together to hold said light emitting device in place, said power switch being mounted in one side of said second socket shell.

3. The aroma diffusing night lamp system as claimed in claim 2, wherein said lamp socket is mounted with a gasket ring and stopped against the bottom edge of said lampshade, the retaining rods of said first socket shell and said second socket shell being inserted through the through hole on the bottom edge of said lampshade and stopped at a top side of the bottom edge of said lampshade after rotation of lamp socket relative to said lampshade through an angle.

4. The aroma diffusing night lamp system as claimed in claim 3, wherein said gasket ring has a bottom ring portion, a top ring portion, an upright stop wall and a hole, said top ring portion being located on a top side of said bottom ring portion, said top ring portion having a relatively smaller diameter than said bottom ring portion so that the periphery of said top ring portion defines said upright stop wall, the hole of said gasket ring extending through said top ring portion and said bottom ring portion at the center, said upright stop wall having a diameter fitting the diameter of the through hole on the bottom edge of said lampshade, said gasket ring being mounted around an upper part of said lamp socket below the retaining rods of said first socket shell and said second socket shell and stopped at the top side of the bottom edge of said lampshade after insertion of the retaining rods of said first socket shell and said second socket shell upwardly through the through hole on the bottom edge of said lampshade and rotation of said lamp socket relative to said lampshade through an angle.

5. The aroma diffusing night lamp system as claimed in claim 1, wherein said electric plug further comprises a gear wheel located on the cylindrical rear side of said electric plug body; said lamp socket has a damping spring leaf mounted in a locating groove in the round hole thereof, said damping spring leaf having a protruding damping portion located on a middle part thereof stopped against the toothed periphery of said gear wheel.

6. The aroma diffusing night lamp system as claimed in claim 5, wherein said damping spring leaf has W-shaped configuration; said locating groove of said lamp socket has a W-shaped configuration fitting the W-shaped configuration of said damping spring leaf.

7. The aroma diffusing night lamp system as claimed in claim 5, wherein said electric plug body has a plurality of retaining blocks equiangularly spaced around the cylindrical rear side thereof for securing said gear wheel.

8. The aroma diffusing night lamp system as claimed in claim 7, wherein the retaining blocks of said electric plug body have a triangular shape; said gear wheel is a gear ring, having a plurality of triangular retaining grooves equiangularly arranged on the inner diameter thereof and respectively forced into engagement with the triangular retaining blocks of said electric plug.

9. The aroma diffusing night lamp system as claimed in claim 5, wherein said lamp socket further comprises a spring holder groove, a set of first metal conducting plates arranged at one lateral side relative to said spring holder groove and electrically connected to one of the positive and negative poles of said light emitting device, a set of second metal conducting plates arranged at an opposite lateral side relative to said spring holder groove and electrically connected to the other one of the positive and negative poles of said light emitting device, a spring member mounted in said spring holder groove, and a metal ball supported on said spring member; said power switch has a cone adapted for moving said metal ball between a first position to electrically connect said set of first metal conducting plates and said set of second metal conducting plates and a second position to electrically disconnect said set of first metal conducting plates from said set of second metal conducting plates.

\* \* \* \* \*